United States Patent [19]
Mccoy

[11] Patent Number: 5,599,337
[45] Date of Patent: Feb. 4, 1997

[54] RAISED CENTER SANITARY NAPKIN WITH RAISED EDGES

[75] Inventor: Sherilyn S. Mccoy, Monmouth Junction, N.J.

[73] Assignee: McNeil-PPC, Inc., Skillman, N.J.

[21] Appl. No.: 236,310

[22] Filed: May 2, 1994

[51] Int. Cl.$^6$ ............................................. A61F 13/15
[52] U.S. Cl. ..................... 604/385.1; 604/387; 604/367
[58] Field of Search ............................... 604/367, 385.1, 604/387

[56] References Cited

U.S. PATENT DOCUMENTS

| | | | |
|---|---|---|---|
| 2,662,527 | 12/1953 | Jacks | 128/290 |
| 3,406,689 | 10/1968 | Hicks | 128/290 |
| 3,575,174 | 4/1971 | Mogor | 604/385.1 |
| 3,696,187 | 10/1972 | Glassman | 264/294 |
| 4,015,604 | 4/1977 | Csillag | 128/287 |
| 4,195,634 | 4/1980 | Di Salvo et al. | 128/290 |
| 4,285,343 | 8/1981 | McNair | 128/287 |
| 4,425,130 | 1/1984 | DesMarias | 604/389 |
| 4,490,147 | 12/1984 | Pierce | 604/378 |
| 4,554,297 | 11/1985 | Dabi | 604/367 |
| 4,589,876 | 5/1986 | Van Tilburg | 604/385 |
| 4,758,406 | 7/1988 | Dabi et al. | 604/367 |
| 5,171,302 | 12/1992 | Buell | 604/385.1 |

FOREIGN PATENT DOCUMENTS 884608  11/1971  Canada .
91412  10/1983  European Pat. Off. .

*Primary Examiner*—John G. Weiss
*Assistant Examiner*—Rob Clarke
*Attorney, Agent, or Firm*—James P. Barr

[57] ABSTRACT

A feature of this invention is the raised longitudinal hydrophobic edges or edge members in combination with the raised central member. Since the raised central member captures the body fluids close to the source of fluid discharge it contains the body fluids in the central portion of the napkin. In addition, the raised hydrophobic longitudinal edges or edge members prevent fluid from wicking through to the undergarment of the user.

13 Claims, 4 Drawing Sheets

RAISED CENTER SANITARY NAPKIN WITH RAISED EDGES

BACKGROUND OF THE INVENTION

The present invention relates to an improved absorbent article and more particularly to an improved sanitary napkin. The absorbent article has both a raised central member and a pair of longitudinal raised hydrophobic edges or edge members.

Conventional full-size sanitary napkins typically include an absorbent element surrounded by a fluid pervious body facing surface and a fluid impervious undergarment facing surface. The sanitary napkin is generally attached to the user's undergarment by pressure sensitive adhesive.

The two most basic functions of a sanitary napkin are to collect menstrual fluid from the user and to prevent soiling or staining (i.e. protect) the user's under and outergarments. Conventional sanitary napkins do not completely fulfill these absorbency requirements because users experience staining of their undergarments.

Although staining occurs at different locations, side staining is the predominant failure location. Some of the different factors that lead to side staining are fluid wicking along the cover fabric or through the absorbent medium to the side edges of the napkin, lack of napkin stability, and improper fit of the napkin.

Previous attempts to address these modes of failure are described in issued patents and publications.

Canadian Patent No. 884,608 (Levesque, issued Nov. 2, 1971) describes an absorbent product having a zone treated so as to be hydrophobic extending from the outer edge of each longitudinal side of an absorbent pad. However, manufacturing this product is problematic. The process of making this entails applying a liquid repellent composition to the longitudinal sides of the pad and compressing the treated margins to distribute this composition throughout the desired hydrophobic zone. When the composition dries, the zone remains hydrophobic. However, the composition requires more time to dry than is available in a commercially viable process. Therefore, in order to maintain a high rate of production the treated products must be stacked and packaged in the wet state. This brings the treated zones of the products into contact with the walls of the packaging material. The liquid repellent then tends to adhere to the packaging as it dries, thus causing the packaging and hydrophobic zone of the pad to become inextricably attached.

U.S. Pat. No. 4,015,604 (Csillag, issued Apr. 5, 1977) describes a product having means for retarding premature failure of the product by leakage of body fluids from the side edges. A narrow zone of the absorbent element along the edges of the absorbent element but spaced away from its periphery is impregnated with hydrophobic material.

Csillag entails the same wetness/drying time encountered with the Levesque patent. Furthermore, Csillag does not address the problems of napkin instability and improper napkin fit.

Some proposed constructions for eliminating side failure suggest using plastic barriers in a "boated" configuration. European Patent Application 091,412 (Mölnlycke published Oct. 12, 1983) describes an absorbent product with a raised midsection and elasticized side edges. In Mölnlycke the elastic edge forms a "bowl" or "boat" surrounding the absorbent body. Because this product design incorporates a unitary absorbent structure having a cover which extends from lateral edge to lateral edge, there is a high propensity for side leakage to occur. This product design is somewhat unstable. Upon compression, the napkin may bunch, causing a depression in its center, and reducing the area of coverage. Additionally, fluid may wick along the cover to the edge of the napkin. Furthermore, the peripheral flange region of the absorbent element may tend to fold in toward the center of the napkin. Fluid then smears onto the outer edge of the flange. The flange may then contact the user's garment, causing soiling.

So called "compound" sanitary napkin designs have also been proposed to combat side failure. U.S. Pat. No. 2,662,527 (Jacks, issued December 1953), describes an absorbent pad having a main body member composed of absorbent material and a second absorbent portion secured on the face of the main member. The second portion is narrower and shorter than the main body member and has dimensions which allow it to fit between the labia. The second portion is intended to be held against the vaginal orifice such that fluid is absorbed at the point of discharge from the body. The bottom section of the napkin is held in place with a sanitary belt or a supporter. Jacks intended the small top pad to provide a damming action to retard leakage of fluid toward the rear of the user. The main body member was to engage the body at a point near the rectum to provide a second damming action. Although this system provides means to capture the fluid, fluid may still flow from the second absorbent portion to the main body member. During use, the longitudinal edge of the main member may fold in and contact the soiled edge of the top member. After returning to its original state, the stained edge of the main member may contact the edge of the undergarment crotch.

Another compound sanitary napkin design having two discrete layers is described in U.S. Pat. No. 3,406,689 (Hicks, issued Oct. 22, 1968). These two pads are separate from one another and are freely movable with respect to each other. The first pad, or contact pad, is intended to be pressed against the body of the user while the second pad extends over the genitalia and anal portions of the user. Both pads contain absorbent material. Positioning and discarding these two pads may be time consuming and messy. Fluid may also travel from the contact pad to the edge of the backup pad, resulting in napkin failure.

U.S. Pat. No. 4,425,130, (DesMarais, issued Jan. 10, 1984) also describes a two-pad napkin design. A primary menstrual absorbent pad and a "panty protector" pad are joined such that there is a continuous section spanning at least 75% of the common length uninterrupted by points of attachment. The primary absorbent pad is intended to absorb and retain menstrual fluid. The panty protector member is meant to protect the user's garments from being soiled by fluids which are expelled from the primary menstrual pad or which inadvertently pass the primary pad. This construction does not compensate for the deficiencies of two-pad systems discussed above.

Structural napkin instability also causes side failure. Compressive forces, such as those exerted by a user's thighs, tend to cause the napkin applied to a napkin, to fold or bunch, reducing the area of coverage and interrupting contact between napkin and body. Thus, body fluid may be deposited on the side edge of the napkin, resulting in napkin failure. U.S. Pat. No. 4,195,634 (Di Salvo, issued Apr. 1, 1980) describes resilient and/or stabilized absorbent systems designed to address this problem. However, Di Salvo does not disclose a raised central member.

Another result of a compressive force is that the undergarment rises up around the sides of the napkin and contacts the napkin face, especially if the width of the undergarment crotch is greater than the sum of the napkin width and the thickness of each edge. McNair, U.S. Pat. No. 4,285,343 and Van Tilburg, U.S. Pat. No. 4,589,876 describe designs that address this mode of failure.

McNair teaches a central elongate absorbent element with laterally extending side panels. The side panels are folded over on the outer surface of the crotch section of an undergarment in order to keep the central element of the napkin from sliding. McNair does not discuss fluid wicking.

Van Tilburg teaches a sanitary napkin that includes a central absorbent pad with flaps extending from each of its longitudinal edges. Each flap has a flexible axis located in the body of the flap which allows the flap to be folded on itself. It is possible for fluid to wick to the longitudinal edges of Van Tilburg. The negative attributes associated with this 2-flap design includes a cumbersome attachment and removal system and lack of comfort for the user during use.

When improper fit of the napkin occurs fluid travels along the body and bypasses the sanitary napkin. When the napkin is away from the user, fluid tends to travel along the contours of the body. The result is that soiling of the user's undergarment crotch may occur at the side edge or at the front and/or back of the undergarment.

In response to the improper fit of napkins some patents discuss napkins in which the central region contains additional absorbent or is thicker than the sides of the napkin. One such patent is Pierce, U.S. Patent No. 4,490,147 which describes a raised center sanitary napkin comprising elongate absorbent pads which are arranged parallel to one another in a pyramid shaped bundle. These pads are moveable with respect to one another and are encased by a liquid pervious cover material. Although there are discrete absorbent zones, the cover encompasses these in such a way that the product functions as a unitary structure. It is possible for fluid to wick along the cover to the napkin edge. Also because of the pyramid shape it is likely that fluid would "roll off" the napkin edge, hence, causing soiling of the user's undergarment. Although this design addresses fit, it does not have the features necessary to provide adequate protection.

U.S. Pat. No. 3,969,187 (Glassman) describes a napkin embodying a longitudinal, centrally located rib or ridge on its top surface adapted to enter the vaginal cleft. The central ridge and the pad surface on either side of the ridge are provided with a multiple of deep spaced-apart channels to increase the lateral compressibility of the marginal surfaces and the ridge. However, there is no provision for preventing side failure.

Another patent that attempts to alleviate the problems that arise from factor three is Mölnlycke, which was discussed above.

SUMMARY OF THE INVENTION

One embodiment of this invention is an absorbent article comprising an elongate napkin base. The napkin base has a body facing surface, a garment facing surface, a front lateral end, a rear lateral end, a raised central member, and first and second fibrous raised hydrophobic longitudinal edges. The thickness of the first and second raised hydrophobic longitudinal edges is greater than the thickness of the elongate napkin base. A central portion of the napkin base is located in between the first and second fibrous raised longitudinal edges.

The distance between the raised central member and the first fibrous raised longitudinal edge is equal to the distance between the raised central member and the second raised longitudinal edge. In addition, the raised central member is parallel to the first and second fibrous raised longitudinal edges. The first and second fibrous hydrophobic longitudinal edges each have an inner wall facing the raised central member base and an outer wall facing away from the raised central member. The inner and outer walls of the first and second edges have an upper portion and a lower portion.

Another embodiment of the present invention is also an absorbent article comprising an elongate napkin base. The elongate napkin base has a body facing surface, a garment facing surface, a front lateral end, a rear lateral end, a first longitudinal edge and a second longitudinal edge. In this embodiment of the present invention the first and second fibrous hydrophobic edge members are separate from the napkin base. The pair of first and second raised hydrophobic longitudinal edge members have a thickness greater than the thickness of the elongate napkin base are attached to the longitudinal edges of the napkin base. A central portion of the napkin base is located in between the first and second raised longitudinal edge members. A central line of juncture is in the central portion. The distance between the central juncture line and the first raised longitudinal edge member is equal to the distance between the central juncture line and the second raised longitudinal edge member. A raised central member is attached to the body facing surface of the elongate napkin base by an attachment means disposed along the central line of juncture. This raised central member is parallel to the first and second raised longitudinal members.

The garment facing surface of the napkin base is attached to a backing layer. The backing layer has a body facing surface, a garment facing surface, a front lateral end and a rear lateral end. The front lateral end extends beyond the front lateral end of the napkin base and the rear lateral end extends beyond the rear lateral end of the napkin base. The first and second hydrophobic longitudinal edge members each have an inner wall facing the raised central member and an outer wall facing away from the raised central member. The inner and outer walls of the first and second edge members all have an upper portion and a lower portion. The upper portion of the first and second edge members is attached with an attachment means to the first longitudinal edge of the elongate napkin base. The lower portion of the first and second edge members is simultaneously attached with an attachment means to the body facing surface of the backing layer.

BRIEF DESCRIPTION OF THE DRAWINGS

FIG. 6 is a cross-sectional view of an embodiment of this invention having triangular raised edges and a triangular raised central member;

FIG. 7 is a cross-sectional view of an embodiment of this invention having rectangular raised edge members and a rectangular raised central member;

FIG. 8 is a cross-sectional view of an embodiment of this invention having elliptical raised edge members and an elliptical raised central member;

FIG. 9 is a cross-sectional view of an embodiment of this invention having round raised edge members, a round raised central member and a napkin base with a groove for the raised central member to mate with;

DETAILED DESCRIPTION OF THE PREFERRED EMBODIMENTS

This invention combines fibrous raised longitudinal hydrophobic edges 130 or edge members 30 with a raised central member. The relationship between the hydrophobic raised edges 130 or hydrophobic raised edge members 30 and the raised central member 20, 20' or 120 are discussed in detail below, with reference to the FIGS. A description of each of the components and its functionality is also included.

It will be understood, however, that these embodiments are merely illustrative of the teachings herein and that the teachings apply with substantial advantage to other similar products. For example, the invention may apply to sanitary napkins of the type well known in the art which comprise an absorbent element completely wrapped in a fluid pervious cover or such a product wherein a fluid impervious layer is incorporated within or immediately adjacent to the surface of the absorbent element. The invention is applicable to other kinds of absorbent products now in use and to be worn against the body such as diapers, incontinence pads, and surgical dressings.

Figure 1:
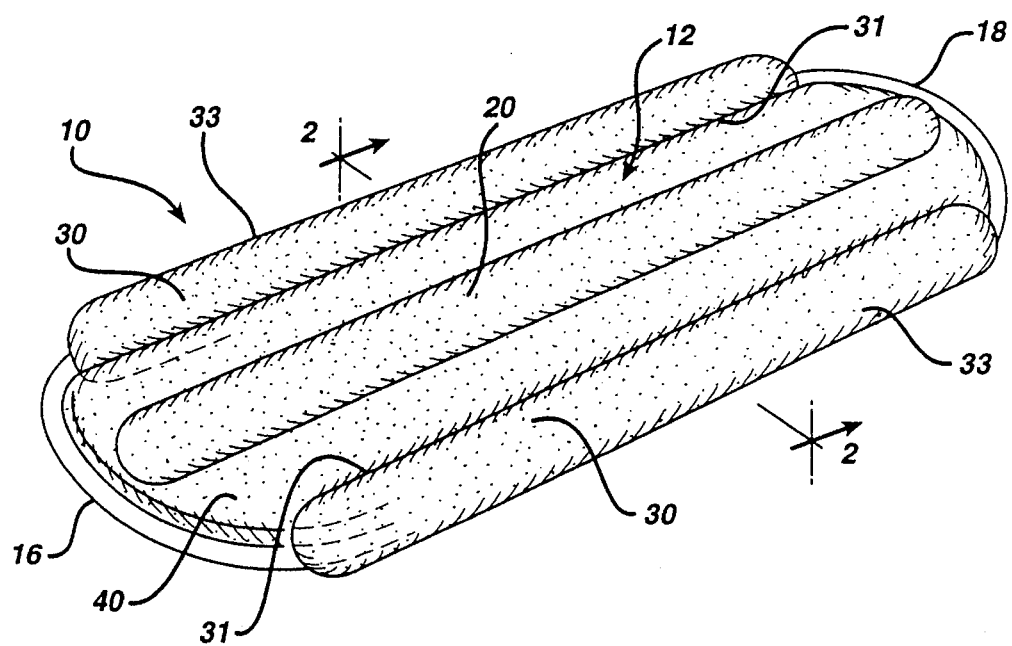
FIG. 1 is a perspective view of a raised center sanitary napkin with raised edge members of one embodiment of the present invention.

The compound sanitary napkin described herein has advantages over the "raised center" and compound napkin systems previously described. This invention provides a system that is readily absorbent and limits the transport of menstrual fluid so the user's undergarment is protected against soiling. A compound sanitary napkin 10 containing a raised central member 20, an elongate napkin base 40, and a pair of longitudinal raised hydrophobic edge members 30, as illustrated in FIG. 1, achieves this.

Figure 3:
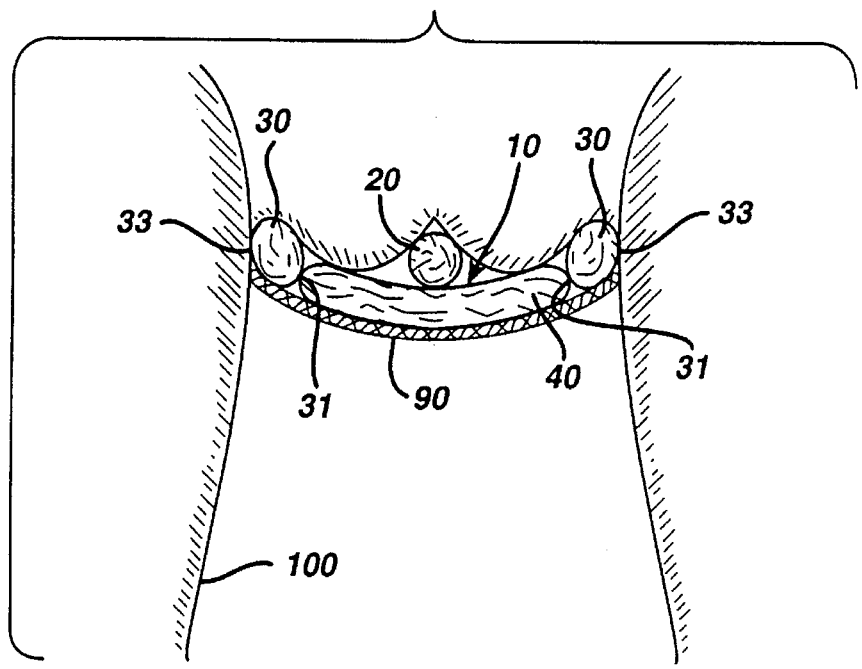
FIG. 3 is a schematic view illustrating the orientation of the napkin when placed during use.

The raised central member 20 absorbs fluid as the user loses it. The raised central member 20 is closer to the source of fluid discharge. This is best illustrated in FIG. 3 where the raised central member 20 is positioned in the vaginal orifice, so fluid is more readily captured and there is less chance for fluid to travel along the body. In the FIGS. features depicted in one embodiment such as raised central member 20 have a "1" placed in front of them when they are illustrated in another embodiment, e.g., raised central member 120. Whenever a description is applicable to more than one embodiment I will use the numbers of the features of all applicable embodiments.

Raised central member 20, 20' or 120 acts to contain the menstrual fluid in the central portion 50 of the napkin 10 or 110. The raised central member also absorbs and contains fluid because of its discrete nature. Also, the raised central member 20, 20' or 120 imparts dimensional stability to the napkin. Due to its thickness and resiliency, raised central member 20, 20' or 120 enhances napkin fit-to-the-body. The napkin base 40 or 140 functions to protect the garments of the user from soiling by absorbing fluids expelled from the raised central member 20, 20' or 120 or fluids that inadvertently bypass the raised central member 20, 20' or 120.

When a compressive force is applied to a discrete raised center napkin, the base of the napkin tends to fold up around the center and engulf it. Deformation in a discrete raised center napkin is different from that of a unitary low density absorbent system. A low density absorbent napkin bunches in accordion-like fashion so the napkin center becomes depressed and the area of coverage is reduced. The central member 20, 20' or 120 of this invention does not collapse to the body. So, the raised central member 20, 20' or 120 in this invention acts as a pivotal point and therefore imparts stability to the napkin 10 or 110.

When a napkin is compressed fluid may transfer from the raised central member to the edge of the napkin base fluid may not be absorbed by the edge. However, body fluid may smear along the surface of a hydrophobic edge. Upon release of this load, the napkin will return back to its original configuration. At that time fluid on the napkin edge may transfer to the undergarment. A hydrophobic edge 30 or edge member 30 with an inner wall 31 or 131 that is thicker than the napkin base 40 or 140 is less likely to transfer to fluid an undergarment. Therefore, raised longitudinal hydrophobic edge 130 or edge member 30 provides a buffer zone of protection. The raised edges 130 or edge members 30 act as spacers between the soiled regions of the napkin 10 or 110 and the undergarment. So, the outer wall 33 or 133 of the raised edge 130 or edge member 30 in contact with the thigh of the user 100 or undergarment edge 90 is shielded from soiling. The inner wall 131 or 31 of the raised edge may be soiled by fluid transferred from the napkin central portion 50 or 150. However, the outer wall, 33 or 133, which is closest to the thigh of the user remains unsoiled.

The raised central member 20, 20' or 120 absorbs and contains fluid which results in napkin 10 or 110 having a cleaner appearance after use. These raised edges also act as gaskets which fit to the contours of the body. They fit against the user's inner thigh region (See FIG. 3) which helps keep the thigh region clean from body fluids.

The edges 130 or edge members 30 may conform to the shape of the user. FIG. 3 illustrates how edge members 30 conform to the shape of the thighs 100 of the user. The thinner napkin base 40 of napkin 10 may provide a comfort benefit versus thicker napkins.

Figure 2:
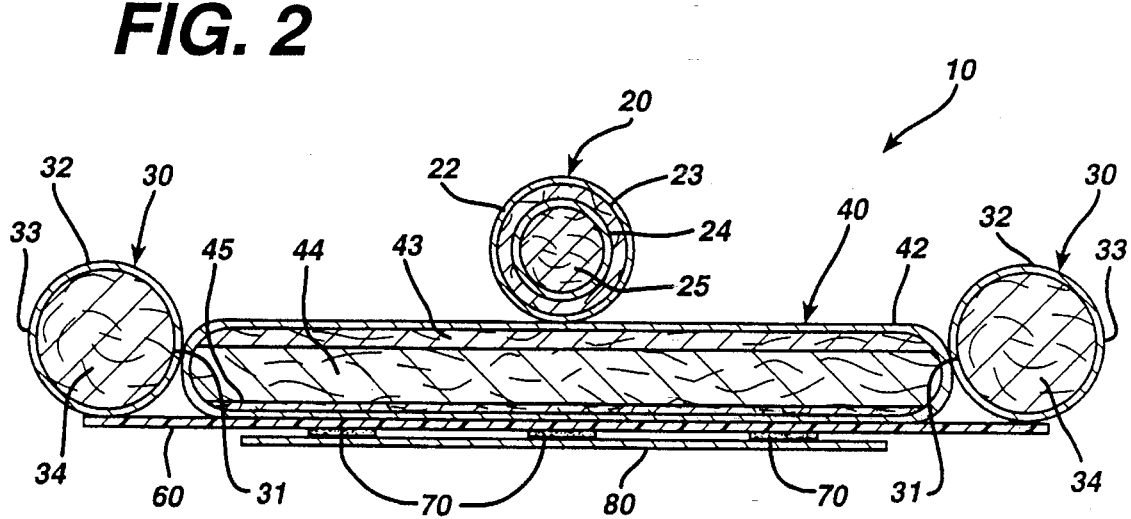
FIG. 2 is a transverse cross-sectional view taken along line 2—2 of FIG. 1.
Figure 10:
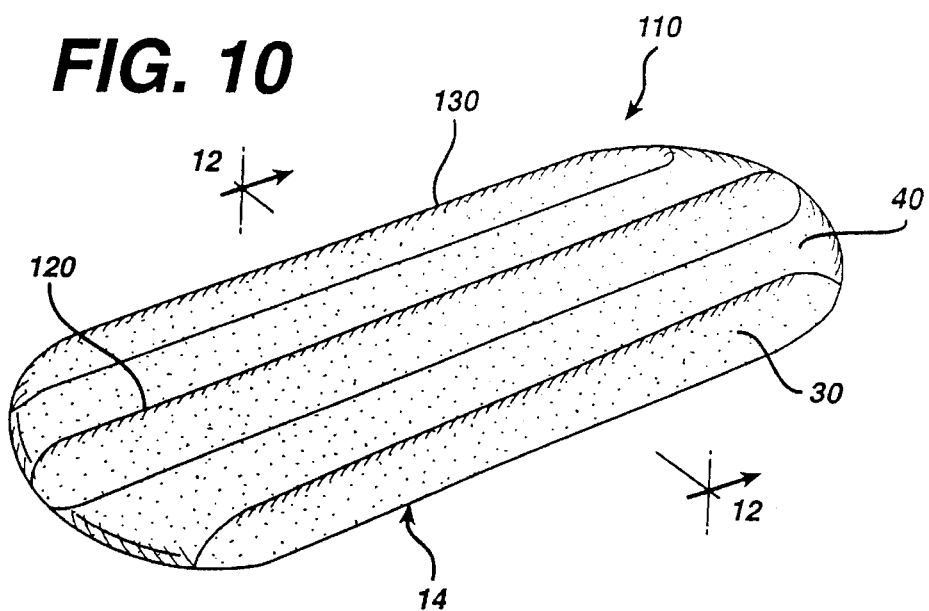
FIG. 10 is a perspective view of another embodiment
Figure 11:
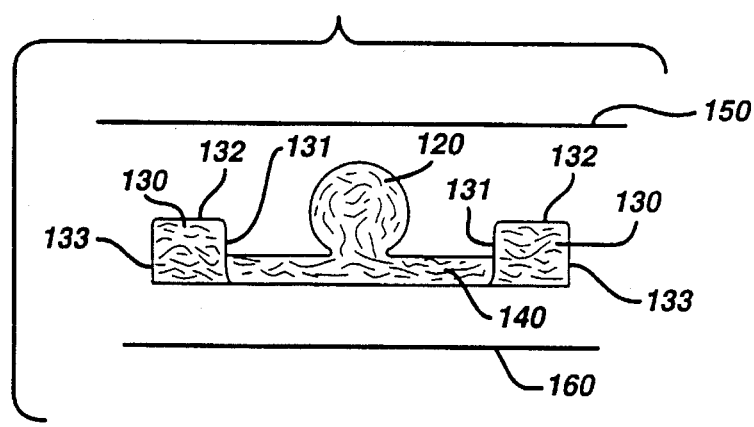
FIG. 11 is an exploded sectional view of another embodiment.
Figure 12:
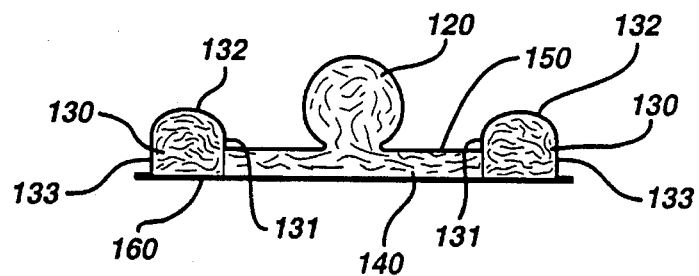
FIG. 12 is a cross-sectional view of another embodiment taken along line 12—12 of FIG. 10.

The napkin 110 of FIGS. 10–12 is a simpler article than the one illustrated in FIG. 2. Napkin 110 is therefore easier to manufacture. On the other hand, napkin 10 of FIG. 2 is more like having both a tampon and a napkin to absorb body fluids. This is because the raised central member 20 is a separate element from the napkin base 40. Raised central member 20 acts like a tampon. Any leakage from raised central member 120 may travel transversely across napkin base 140. However, such leakage will not pass from the inner walls 131 of raised edges 130 to their outer walls 132. Therefore, possible soiling of the undergarments of the user will be decreased.

Figure 4:
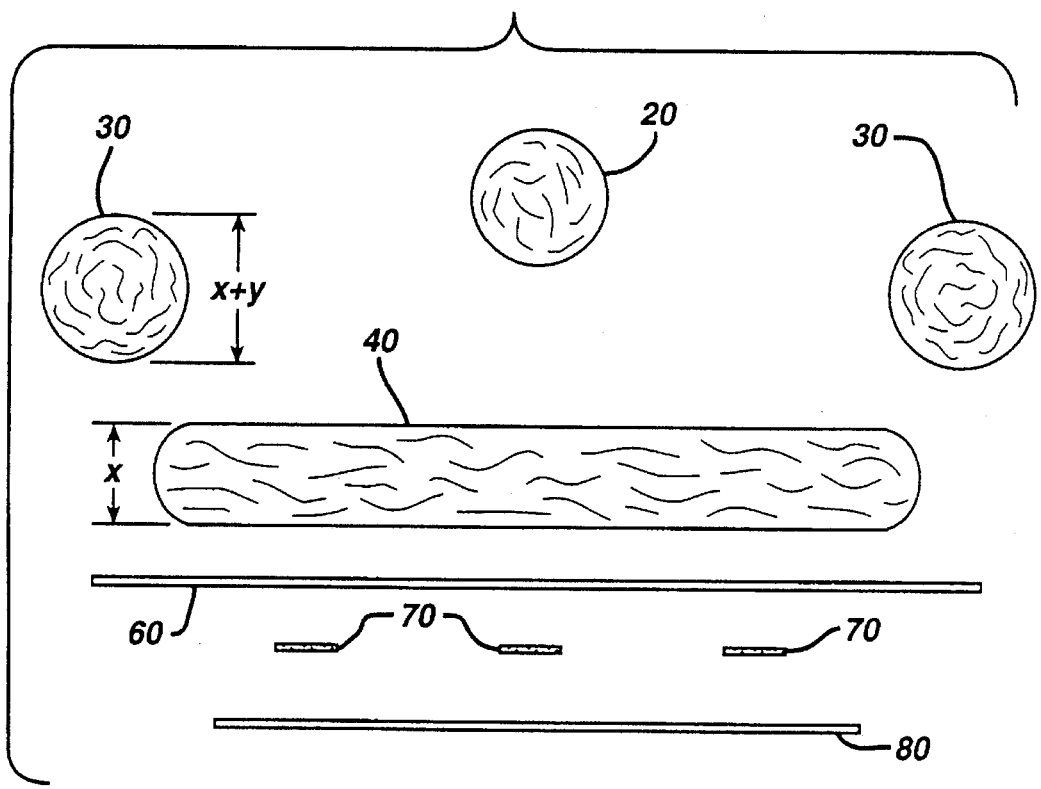
FIG. 4 is a schematic exploded view of the elements depicted in FIG. 2.

FIG. 4 illustrates how the separate elements of the embodiment of FIG. 1 are to be assembled. Since the napkin 10 of one embodiment has separate raised edge members 30 and a separate napkin base 40, backing layer 60 is needed to hold the raised edge members 30 next to the napkin base 40 along their inner and outer lower portions 36 and 38. An adhesive means 70 is placed on the garment facing surface of backing layer 60 in order to adhere napkin 10 to the user's undergarment. Release paper 80 protects adhesive means 70 before use.

In the embodiment of napkin 110 illustrated in FIGS. 11 and 12 raised edges 130 are an extension of the napkin base 140 and are surrounded on their inner and outer walls 131 and 133 by a cover 132 that is composed of hydrophobic material. This is to prevent contact of body fluid with the user's undergarment.

It is preferred that napkin base 40 or 140 be thinner than raised edges 130 or raised edge members 30. The thinner napkin base 40 or 140 may provide a comfort benefit that thicker napkins do not provide. The fluid impervious barrier can be of the same dimensions as the absorbent or it may be wider and longer. Conventional plastic and/or breathable barriers may be utilized.

Raised central member 20 of FIGS. 3, 4, 11 and 12 is constructed of one material. The raised central member 20 should be absorbent and have the ability to decrease the transport of fluid. Raised central member 20 should be separate from base 40 if possible. FIGS. 11 and 12 show embodiments of napkin 110 that have raised central members 120. These raised central members 120 are an integral part of the napkin base 140. The unitary absorbent article 110 has a cover 150 that surrounds both the body facing surface of the raised central member 120 and the napkin base 140. Other embodiments illustrated in FIGS. 1–4, 6–9 include a separate raised central member 20 that is attached to the cover 42 of napkin base 40.

Stabilizers may be inside raised central member 20, 20', or 120 in any shape. Indeed, since raised central member 120 is integral with napkin base 140 a stabilizing means in the shape of a cross or a "T" may help hold raised central member 120 and napkin base 140 together. In such a configuration the top portion of the "T" is in raised central member 120 and the bottom portion of the "T" extends down from raised central member 120 into napkin base 140. It is also possible to invert the "T" shaped stabilizer or use a stabilizer in the shape of a "Y" or other letters, geometric shapes, etc.

Figure 5:
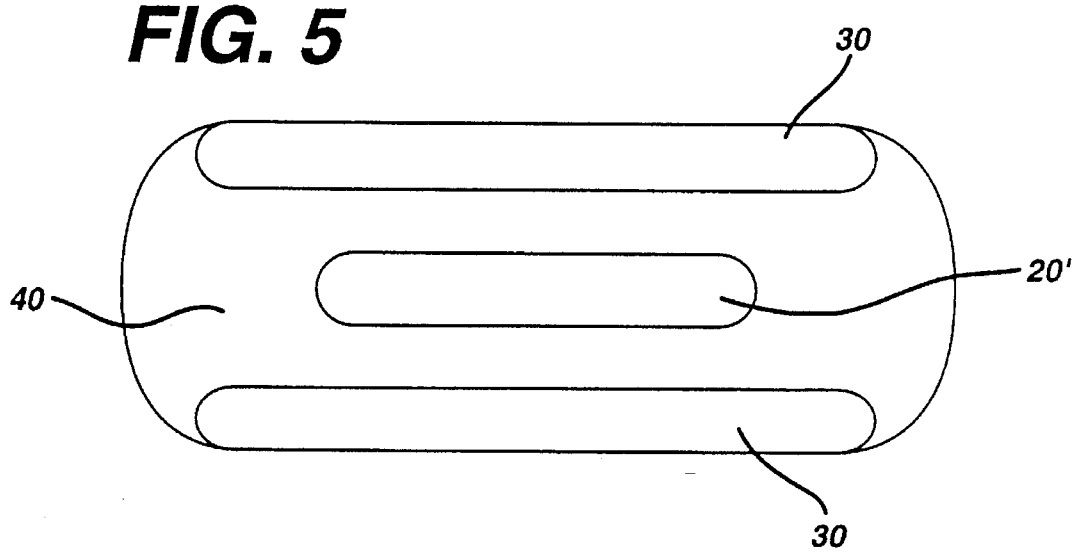
FIG. 5 is a top plan view of another embodiment of this invention.
Figure 6:
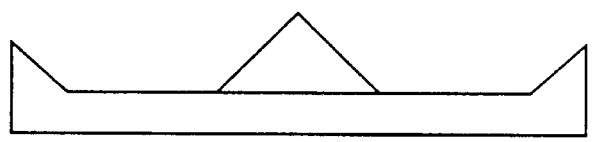
FIGS. 6–9 are schematic sectional views of different embodiments of this invention.
Figure 7:
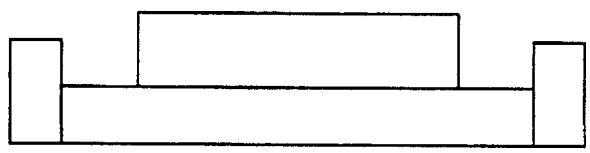
Figure 8:
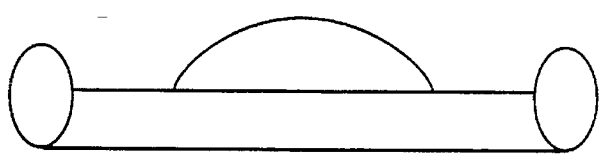
Figure 9:
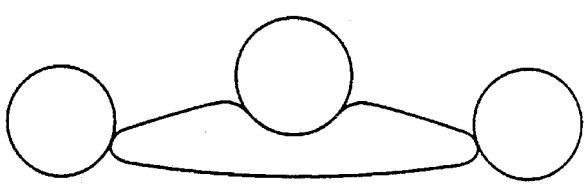

The length of this raised central member 20 may be of any convenient dimension. However, the width at the widest portion of the raised central member 20 must not exceed the overall width of the napkin base 40. FIG. 5 illustrates a raised central member 20' whose length is less than the length of the raised hydrophobic edges 30. The cross-section of the raised central member may be of any shape, such as circular, rectangular, oval, triangular, etc., as illustrated by FIGS. 6, 7, 8 and 9. Raised central member 20 may be joined to base 40 by means of a continuous or discontinuous line of juncture. This joining may be achieved though adhesive means, heat sealing, ultrasonic sealing, etc.

The raised central member 20 or 120 optionally has a cover 22 or 122. Like absorbent core 46 raised central member 20, 20' or 120 may contain a single component 22 or 122 or it may contain multi-layers as illustrated in FIG. 2. FIG. 2 illustrates a raised central member 20 containing multiple layers 23, 24 and 25. Every layer 23, 24 and 25 need not be absorbent as long as the raised central member 20 has overall absorbent properties. For example, a nonabsorbent material may be used in layer 25 of raised central member 20 to enhance resiliency. A range of materials such as fiber, foam, fabric, super absorbents, etc. may be used in the construction of this raised central member 20, 20' or 120.

The base 140 or 40 optionally has a cover 42. For the embodiments that have a cover 42 both the cover fabric 42 and the pulp material may be selected from any of the many conventional materials known in the sanitary napkin art as being used for these purposes. The cover fabric of cover 42 may be selected from those fluid-permeable materials which allow menstrual fluids to flow to the absorbent core 46, while making the napkin 10 or 110 feel dry when it is in use. For example, the absorbent core material 46 may be formed from a non-woven rayon or polypropylene material.

Napkin base 40 or 140 has an absorbent element and a moisture barrier. Furthermore, napkin base 140 and 40 may be of any length or width and/or vary in thickness in the x and/or y directions. The napkin base 40 or 140 should protect the user's undergarment from soiling. Napkin base 40 does this by absorbing fluid which is expelled from raised central member 20, 20' or 120 or which bypasses.

The napkin base 40 of FIGS. 1–8 and 140 of FIGS. 10–12 is a conventional elongate absorbent napkin base. However, the napkin base of FIG. 9 has a groove with which the raised central member mates.

The absorbent core 46 may be a wood pulp fluff, rayon fiber material, cotton, mixtures of rayon and cotton, tissue wadding or any of the many other conventional absorbing materials used in sanitary napkins. The absorbent core 46 may consist of a single ply or a multitude of layers, such as absorbent layers 43, 44 and 45 illustrated in FIG. 2. The layers 43, 44 and 45 may be of the same type of material or, may be made of materials varying in density, composition, and absorbency. Superabsorbents, foams, and fibers may constitute one or more of these absorbent layers, 43, 44 and 45.

The raised hydrophobic edge 130 or edge member 30 of the napkins 110 or 10 of this invention limit soiling of the undergarment of the user. The thickest portion of the raised edges 130 or edge members 30, are preferably greater than the thickest portion of the napkin base 140 or 40. FIGS. 2, 4 and 6–9 illustrate embodiments that have discrete raised edge members 30.

The fibrous hydrophobic edges 130 or edge members 30 allow fluid to penetrate into the interstices of the structure. Therefore, smearing of fluid on the edge 130 or edge member 30 is limited.

FIGS. 11 and 12 illustrate hydrophobic raised edges 130 that are integral with napkin base 140 or 40. In particular, FIG. 4 illustrates that raised edges 30 are thicker than napkin base 40 by a thickness "y". Therefore, when the napkin 10 is compressed, the inner wall 36 of raised longitudinal hydrophobic edge members 30 pick up fluid. However, the outer walls 38 of the raised edges 130 and raised edge members 30 are protected. The angle formed by a line tangent to an inner wall 36 of the raised edge 130 or edge member 30 and a plane parallel to the line tangent to the highest point of the napkin base 140 or 40 must not equal 0°. It is desirable that this angle be between 20° and 160°. The raised edge 130 or raised edge member 30 is preferably hydrophobic and nonwicking in nature. The raised edges 130 or edge members 30 are fibrous to reduce smearing of fluid along the inner and outer walls 31 and 33. A fibrous raised edge 130 or edge member 30 feels dry and clean to the user.

Discrete fibrous hydrophobic raised edge members 30 are attached to napkin base 40. The width of edge member 30 should be between 0.125 inch and 1.25 inches. These edge members 30 extend substantially the full length of napkin 10 as seen in FIGS. 1 and 5. Raised edges 130 also extend substantially the full length of napkin 110 in FIG. 10. Edge members 30 or edges 130 may be present only in central portion 50 of napkin 10.

The two raised longitudinal edge members 30 or edges 130 also provide a comfort benefit to the user. To enhance user comfort, the raised edges 130 or edge members 30 should be soft and resilient. Materials such as hydrophobic foams may be used in raised edges 130 or edge members 30. These edges 130 or edge members 30 may or may not be enclosed by a cover 32.

The attachment system may be of any conventional materials such as adhesive means 70, best illustrated in FIG. 4. Adhesives, also shown in FIG. 2 are commonly used to secure sanitary napkins to the inner crotch area of the garments of the user. Napkin 10 may also be secured to the body of the user through use of a sanitary belt or tabs.

As the pressure sensitive adhesive for this invention, any of the polymeric adhesives known to those skilled in the art can be used. Some examples include styrenebutadiene rubber, polyvinyl ethers, polyesters of acrylic acid and polyisobutylene. The track adhesive means in accordance with this invention may consist of numerous different shapes and sizes many of which are well known in the art.

The advantages of the instant invention can be better understood by reference to the following Examples.

EXAMPLE 1

Table 1 contains a description of one possible embodiment of a raised central member, raised longitudinal hydrophobic edge member design.

TABLE 1

Description of Raised Center
Sanitary Napkin with Raised Edges

| Component | Description | Configuration |
|---|---|---|
| Raised Central Member: | | |
| Cover | 2 oz./yd² FFWP[1] | 4" × 9" C-folded around absorbent |
| Absorbent | Low Density Pulp | 2" × 6" |
| | High Density Pulp/SA (12% Sanwet 1M1OOO) | 2" × 6" |
| Resilient Core | 50/50 "ENKA"/Hollofil Resilient Fabric | Insert ½" × ½" × 6" |
| Napkin Base: | | |
| Cover | 0.5 oz./yd² "ENKA" Fusible Fiber Coembossed To 2.0 oz./yd² FFWP | 4.25" × 9" C-folded around absorbent |
| Absorbent | Low Density Pulp | 2" × 7" |
| | High Density Pulp/SA (12% Sanwet 1M1OOO) | 2" × 7" |
| Raised Hydrophobic Edges Members: | 50/50 "ENKA"/Hollofil Resilient Fabric wrapped individually in 0.5 oz./yd² "ENKA" Fusible Fiber Cover | 0.3" × 8" |
| Barrier: | Polyethylene | 2.5" × 9" |
| Construction Adhesive: | Hot Melt Laminating Emulsion Adhesive | Continuous Lines |
| Positioning Adhesive: | Pressure Sensitive Hot Melt Adhesive | 3 Lines (0.25" × Spaced 0.25" Apart |
| Release Paper | Silicone Coated Paper | |

[1] a fusible fiber, wood pulp, polyester Hollofil blend
*Configuration of the components used to manufacture the product.

The dimensions of this embodiment were determined to be:

| Dimensions (in.) N = 30 | Avg. Dimensions of 30 Raised Center Sanitary Napkins |
|---|---|
| Total Product | |
| Length | 8.8 |
| Width | 2.7 |
| Thickness | |
| Center | 1.0 |
| Base | 0.2 |
| Raised Edge | 0.4 |
| Dimensions (in.) N = 30 | Avg. |
| Raised Central Member | |
| Length | 8.8 |
| Width | 1.2 |
| Circumference | 3.8 |
| Absorbent Napkin Base | |
| Length (Overall) | 8.8 |
| Length of Absorbent | 7.2 |
| Width | 2.0 |
| Raised Longitudinal Edge | |
| Length | 8.0 |
| Width | 0.3 |

The average napkin weight was 16 grams.

The embodiment illustrated in FIG. 2 may have the materials described below. FIG. 2 illustrate the napkin 10 described in Table 1 above, as discussed above with reference to the individual components; the raised hydrophobic edge members, the raised central member, the napkin base 40 and the backing layer 60.

FIG. 2 illustrates an embodiment of the napkin 10 described in TABLE 1 of Example 1. As illustrated in FIG. 2 and described in TABLE 1 the napkin base 40 has a cover 42 that is made of 0.5 oz./yd² "Enka" Fusible Fiber Coembossed with 2.0 oz./yd² FFWP. The layer 43 of absorbent next to the cover 42 is low density pulp. Inside the layer 43 of low density pulp is a layer 44 high density pulp/SA (12% Sanwet 1M1OOO).

The raised central member 20 of FIG. 2 has a cover 22 which is 2 oz./yd² FFWP as stated in Table 1 of Example 1. The outermost layer of material next to the cover 22 is an absorbent 23 which is low density pulp. The layer of absorbent adjacent to and inside absorbent 23 is high density pulp/SA (12% Sanwet 1M1OOO) indicated by reference numeral 24. The resilient core 25 is 50/50 "Enka"/Hollofil Resilient Fabric.

The raised hydrophobic edge members 30 of Example 1 have a cover 32 made of 50/50 "Enka"/Hollofil Resilient Fabric wrapped individually in 0.5 oz./yd² "Enka" Fusible Fiber Cover.

EXAMPLE 2

Another embodiment of this invention is similar to Example 1, however, the raised central member 20 has dimensions of 1"×4". It is secured to the napkin base 40 only at the ends of the center. The raised central member 20 consists of pulp with a core of amino-ether foam, such as the amino-ether foam described in U.S. Pat. No. 4,554,297 (Personal Products Company) the disclosure of which patent is hereby incorporated herein for reference.

EXAMPLE 3

Yet another embodiment of this invention is similar to Example 2. The difference is that the raised central member 20 of Example 3 consists of pulp with a core of foam-fiber composite such as the composite disclosed in U.S. Pat. No. 4,758,466 (Personal Products Company), the disclosure of which patent is hereby incorporated herein by reference.

EXAMPLE 4

TABLE 2

| Component | Description |
| --- | --- |
| Raised Central Member (1" × 9" long) | |
| Cover | 0.5 oz./yd$^2$ "ENKA" Fusible Fiber |
| Absorbent | Pulp |
| Stabilizing Insert | 50/50 "ENKA"/Hollofil Resilient Fabric |
| Napkin Base (3" × 9" long) | |
| Cover | Same cover as Raised Center |
| Absorbent | Pulp compressed to 0.12" thick |
| Raised Hydrophobic Edges (¼" × 9" long) | 50/50 "ENKA"/Hollofil Resilient Fabric |

Barrier, Construction Adhesive, Positioning Adhesive and Release Paper are conventional sanitary napkin materials.

The embodiment illustrated in FIGS. 11 and 12 may have the materials described below.

The raised hydrophobic edges 130 are composed of 50/50 Enka/Hollofil Resilient Fabric. The cover 142 for napkin base 140 is 0.5 oz/yd$^2$ "ENKA" Fusible Fiber. The absorbent of napkin base 140 is pulp compressed to 0.12" thick. The raised central member has a cover made of 0.5 oz./yd$^2$ "Enka" Fusible Fiber. The absorbent in Example 4 is pulp. A stabilizing insert of 50/50 Enka/Hollofil Resilient Fabric is added.

EXAMPLE 5

TABLE 3

| Raised Central Member (1" × 9" long) | |
| --- | --- |
| Cover | 0.5 oz./yd$^2$ "ENKA" Fusible Fiber |
| Absorbent | Pulp/Pulpex (15%) |
| Napkin Base (2.7" × 9" long) | |
| Cover | Same as raised center |
| Absorbent | Same as raised center except compressed |
| Raised Hydrophobic Edge | Pulp/Pulpex covered by Polyethylene Boat |

Barrier, Construction Adhesive, Positioning Adhesive and Release Paper are conventional sanitary napkin materials.

The embodiments illustrated in FIGS. 11 and 12 may have the materials described above.

The raised hydrophobic edges 130 are composed of Pulp/Pulpex covered by Polyethylene Boat. The cover 142 for napkin base 140 is 0.5 oz/yd$^2$ ENKA Fusible Fiber. The absorbent of napkin base 140 is Pulp/Pulpex (15%) and is stabilized pulp. Pulp/pulpex (15%) makes the raised central member 120 more stable, thereby resulting in greater napkin stability. Raised central member 120 has a cover 150 made of 0.5 oz./yd$^2$ "ENKA" Fusible Fiber and contains the absorbent Pulp/Pulpex (15%) which is a stabilized pulp. The absorbent of napkin base 140 is Pulp/Pulpex (15%) and is stabilized pulp.

What is claimed is:

1. An absorbent article comprising:
    a. an elongate napkin base having a body facing surface, a garment facing surface, a front lateral end, a rear lateral end, a raised central member, a first fibrous raised hydrophobic longitudinal edge and a second fibrous raised hydrophobic longitudinal edge;
    b. the first and second raised fibrous longitudinal edges having a thickness greater than the thickness of the elongate napkin base;
    c. the napkin base having a central portion located in between the first and second fibrous raised longitudinal edges;
    d. the raised central member parallel to the first and second fibrous raised longitudinal edges, the distance between the raised central member and the first raised longitudinal edge being equal to the distance between the raised central member and the second raised longitudinal edge;
    e. the first hydrophobic longitudinal edge having an inner wall facing the raised central member and an outer wall facing away from the raised central member;
    f. the second hydrophobic longitudinal edge having an inner wall facing the raised central member and an outer wall facing away from the raised central member;
    g. the inner wall of the first edge having an upper portion and a lower portion;
    h. the outer wall of the first edge having an upper portion and a lower portion;
    i. the inner wall of the second edge having an upper portion and a lower portion;
    j. the outer wall of the second edge having an upper portion and a lower portion.

2. An absorbent article according to claim 1 wherein said central member is cylindrical.

3. An absorbent article according to claim 1 wherein said raised central member is elongate.

4. An absorbent article according to claim 3 wherein the cross-section of said raised central member is triangular.

5. An absorbent article according to claim 3 wherein the cross-section of said raised central member is rectangular.

6. An absorbent article according to claim 3 wherein the cross-section of said raised central member is elliptical.

7. An absorbent article according to claim 1 wherein said napkin base has a cover.

8. An absorbent article according to claim 1 wherein said raised central member contains amino-ether foam.

9. An absorbent article according to claim 1 wherein said raised central member contains a foam-fiber composite.

10. An absorbent article according to claim 1 wherein raised central member includes a stabilizing means.

11. An absorbent article comprising:
    a. an elongate napkin base having a body facing surface, a garment facing surface, a front lateral end, a rear lateral end, a first longitudinal edge and a second longitudinal edge;
    b. a pair of first and second raised hydrophobic longitudinal edge members having a thickness greater than the thickness of the elongate napkin base are attached to the longitudinal edges of the napkin base;

c. the napkin base having a central portion located in between the first and second raised longitudinal edge members;

d. a central line of juncture located in the central portion;

e. a raised central member is attached to the body facing surface of the elongate napkin base by an attachment means disposed along the central line of juncture parallel to the first and second raised longitudinal members, the distance between the central juncture line and the first raised longitudinal edge member being equal to the distance between the central juncture line and the second raised longitudinal edge member;

f. the garment facing surface of the napkin base attached to a backing layer having a body facing surface, a garment facing surface, a front lateral end extending beyond the front lateral end of said napkin base and a rear lateral end extending beyond the rear lateral end of said napkin base;

g. the first hydrophobic longitudinal edge having an inner wall facing the raised central member and an outer wall facing away from the raised central member;

h. the second hydrophobic longitudinal edge having an inner wall facing the raised central member and an outer wall facing away from the raised central member;

i. the inner wall of the first edge member having an upper portion and a lower portion;

j. the outer wall of the first edge member having an upper portion and a lower portion;

k. the inner wall of the second edge member having an upper portion and a lower portion;

l. the outer wall of the second edge member having an upper portion and a lower portion;

m. the upper portion of the first edge member is attached with an attachment means to the first longitudinal edge of the elongate napkin base while the lower portion of the first edge member is simultaneously attached with an attachment means to the body facing surface of the backing layer;

n. the upper portion of the second edge member is attached with an attachment means to the second longitudinal edge of the elongate napkin base while the lower portion of the second edge member is simultaneously attached with an attachment means to the body facing surface of the backing layer.

12. An absorbent article according to claim 11 wherein said central line of juncture is discontinuous.

13. An absorbent article according to claim 11 wherein said central line of juncture is continuous.

* * * * *